United States Patent
Hanson et al.

(10) Patent No.: US 9,056,063 B2
(45) Date of Patent: Jun. 16, 2015

(54) NATURAL SUNSCREEN COMPOSITION

(71) Applicants: James E. Hanson, Chester, NJ (US); Cosimo Antonacci, East Hanover, NJ (US)

(72) Inventors: James E. Hanson, Chester, NJ (US); Cosimo Antonacci, East Hanover, NJ (US)

( * ) Notice: Subject to any disclaimer, the term of this patent is extended or adjusted under 35 U.S.C. 154(b) by 0 days.

(21) Appl. No.: 13/795,305

(22) Filed: Mar. 12, 2013

(65) Prior Publication Data

US 2013/0243709 A1 Sep. 19, 2013

Related U.S. Application Data

(60) Provisional application No. 61/685,166, filed on Mar. 13, 2012, provisional application No. 61/685,460, filed on Mar. 19, 2012, provisional application No. 61/690,257, filed on Jun. 23, 2012, provisional application No. 61/690,280, filed on Jun. 23, 2012.

(51) Int. Cl.
| | | |
|---|---|---|
| *A61K 36/185* | (2006.01) | |
| *A61K 36/82* | (2006.01) | |
| *A61K 36/38* | (2006.01) | |
| *A61K 36/84* | (2006.01) | |
| *A61K 36/54* | (2006.01) | |
| *A61K 8/97* | (2006.01) | |
| *A61Q 17/04* | (2006.01) | |

(52) U.S. Cl.
CPC .. *A61K 8/97* (2013.01); *A61Q 17/04* (2013.01)

(58) Field of Classification Search
CPC .......................... A61K 2300/00; A61K 45/06
USPC .................................................. 424/725, 400
See application file for complete search history.

(56) References Cited

U.S. PATENT DOCUMENTS

| 4,793,990 A | 12/1988 | Grollier et al. | |
|---|---|---|---|
| 5,876,736 A | 3/1999 | Cohen et al. | |
| 6,015,548 A | 1/2000 | Siddiqui et al. | |
| 6,524,599 B2 | 2/2003 | Pinnell | |
| 6,586,018 B1 | 7/2003 | Fasano | |
| 6,830,746 B2 * | 12/2004 | SaNogueira et al. | 424/59 |
| 7,374,748 B2 | 5/2008 | Di Pierro | |
| 7,731,942 B2 | 6/2010 | Golz-Berner et al. | |
| 8,216,555 B2 | 7/2012 | Nieuwenhuijsen | |
| 8,337,820 B2 | 12/2012 | Nieuwenhuijsen | |
| 2004/0096418 A1 | 5/2004 | Gafner et al. | |
| 2008/0175802 A1 | 7/2008 | Di Pierro | |
| 2010/0028276 A1 * | 2/2010 | Grune | 424/59 |
| 2011/0212197 A1 | 9/2011 | Kreuter | |
| 2011/0229538 A1 | 9/2011 | Matravers et al. | |
| 2011/0286946 A1 * | 11/2011 | Oliphant et al. | 424/60 |
| 2012/0195839 A1 * | 8/2012 | He et al. | 424/59 |

FOREIGN PATENT DOCUMENTS

| CN | 101199787 A | 6/2008 |
|---|---|---|
| EP | 952839 B1 | 1/2002 |
| EP | 1301194 A1 | 4/2003 |
| EP | 1837053 A1 | 9/2007 |
| RU | 2259814 C2 | 9/2005 |
| RU | 2458677 C1 | 8/2012 |
| SU | 1327889 A1 | 8/1987 |

OTHER PUBLICATIONS

PCT International Search Report and Written Opinion; PCT/US 2013/030799; Oct. 2, 2013; (7 pgs).

\* cited by examiner

*Primary Examiner* — Chris R Tate
*Assistant Examiner* — Randall Winston
(74) *Attorney, Agent, or Firm* — Gearhart Law LLC

(57) ABSTRACT

A composition for sunscreen or sunscreen enhancer is disclosed. The composition includes UV-blocking component comprising natural extracts, natural oils or nutrients or a combination of these. The composition is capable of protecting skin from the harmful effects of UV-light and it is capable of acting as an enhancer of sunscreen actives, such as zinc oxide, titanium dioxide or other sunscreen actives, such as Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O or Trolamine salicylate.

21 Claims, No Drawings

NATURAL SUNSCREEN COMPOSITION

PRIORITY

This application claims priority of U.S. provisional application No. 61/685,166 filed on Mar. 13, 2012; U.S. provisional application No. 61/685,460 filed on Mar. 19, 2012; U.S. provisional application No. 61/690,257 filed on Jun. 23, 2012 and U.S. provisional application No. 61/690,280 field on Jun. 23, 2012, the contents of each of which are incorporated herein by reference.

FIELD OF THE INVENTION

The invention relates to a cosmetic composition. More particularly the invention relates to a natural sunscreen composition, a natural sunscreen enhancer or booster and method of producing natural sunscreens or sunscreen enhancers and boosters.

BACKGROUND OF THE INVENTION

Human skin can be damaged by solar rays. Overexposure to sun can cause simple sunburn or erythema, along with burns of varying severity. Additional unwanted effects of overexposure to solar radiation include tanning, age spots, immune system suppression, photo-sensitivity and photo allergies. Sun exposure can cause the skin to lose elasticity and form wrinkles, yielding prematurely aged skin. In extreme cases, skin cancer is associated with long-term over-exposure to solar radiation.

It has been estimated that the majority of sun related damage to the skin over a lifetime is the result of outdoor exposure to the sun's ultraviolet rays. The wavelengths relevant to sun related damage include the UV-A, UV-B and UV-C regions. UV-C region is at the shortest wavelength (100-280 nm) with the highest energy content, yet very little of UV-C rays pass through the atmosphere to reach the surface of the Earth. The UV-C rays along with the UV-B rays (280-320 nm) indirectly cause sun tanning and are most likely the source of skin cancers. The longer-wavelength (320-400 nm) UV-A rays directly cause sun tanning, collagen damage and other harmful effects. It should be noted that ~98% of the sun's rays that reach the earth are UV-A rays. Commercially available sunscreen compositions offer a solution to the harmful effects of over-exposure to these ultraviolet rays. However, due to changing atmospheric conditions, increasing number of skin cancer incidents, and increasing awareness of the problem, there is a continuous need of new sunscreen formulations. Especially, there is an increasing need for sunscreen compositions with natural ingredients.

Topical application of sunscreen formulations is well known in the art. Sunscreen active ingredients are generally classified as organic or inorganic. Organic sunscreen agents absorb strongly over a range of UV wavelengths but are transparent to visible light. Some organic active ingredients of sunscreens (Oxybenzone, for example) are known to cause photo-allergic reactions, while others are suspected as estrogen disrupters. Inorganic sunscreen agents such as zinc oxide or titanium dioxide at higher levels leave visible residue referred to as whitening of the skin. Allergic reactions to zinc oxide and titanium dioxide are also known. These sunscreen active ingredients may also enhance the production of reactive oxygen species in the skin, which can produce skin damage.

To overcome these undesirable side effects of organic and inorganic sunscreen agents, there is a need for new formulations that can protect the skin from the harmful effects of ultraviolet radiation without any undesirable side effects.

Certain natural ingredients are known to have sunscreen activities.

U.S. Pat. No. 6,440,402 discloses a synergistic effect of *Kaempferia galanga* (ginger) root extract in sunscreen formulation. The patent also discloses a method comprising the introduction of an amount of extract of *Kaempferia galanga* into a composition sufficient to enhance the photostability of other sunscreen ingredients.

U.S. Pat. No. 8,337,820 and U.S. Pat. No. 8,216,55 both disclose formulation for protecting skin from UV-radiation, where the main ingredients of the composition are titanium dioxide and 5-hydroxy-tryptophan in the form of *Griffonia simplicifolia*-extract. In this preparation *Griffonia simplicifolia* extract is at least partially added due to its brown color to blend the white color of titanium dioxide.

In the art of sun protecting compositions, also compositions containing extracts of green tea, *Aloe vera*, calendula, chamomile and rosemary are known.

Additionally there are various disclosures where general skin care compositions include one or more plant extracts.

U.S. Pat. No. 7,731,942 discloses sun-protecting products containing caffeine, algal extracts, pineapple extract and other ingredients.

U.S. Pat. No. 6,524,599 discloses a composition for skin, nail and hair care where the composition contains milk thistle (*Silibum marianum*) with soybean protein and alpha tocopherol.

U.S. Pat. No. 5,876,736 discloses a skin care composition for revitalizing the skin and comprising plant polysaccharides among various other ingredients.

US patent application 2004/0096418 discloses a composition to lighten the skin color and comprising various plant extracts, including extract from common yarrow (*Achillea millefolium*).

US Patent Application number 2011/0229538 discloses a total skin care composition containing a combination of ascorbic acid and herbal extracts. It should be noted that the herbal extracts and nutrients are not specifically stated to function in the composition as a sunscreen, sunscreen enhancer or sunscreen booster activity. The herbal extracts include red clover extract, ginseng and St John's wort among other extracts.

Furthermore, there are disclosed compositions for different kinds of medical conditions where plant extracts and plant based ingredients are included.

For example European Patent publication EP1301194 discloses treatment of cancerous condition with essential oils including oil of *Ravensara aromatica*.

European Patent publication EP 0952839 discloses a composition to treat burns, where the composition comprises St John's wort, and yarrow among other ingredients.

US application publication 2011/0212197 discloses a composition to treat viral conditions, where the compositions include yarrow extract.

U.S. Pat. No. 6,586,018 discloses a composition for treating premenopausal syndromes including red clover extract among other plant extracts.

Given the present background on sunscreens, the present invention has been created to enhance the effects of currently accepted methods for UV screening. The instant invention provides a sunscreen and sunscreen booster or enhancer comprising natural ingredients.

SUMMARY OF THE INVENTION

It is an object of this invention to provide a topical sunscreen comprising natural ingredients.

It is another object of this invention to provide a composition for a sunscreen booster or enhancer comprising natural ingredients.

It is yet another object of this invention to provide a composition effective in protecting from harmful effects of UV-radiation, where the composition comprises natural extracts, nutrients or oils.

It is yet another object of this invention to provide a method of enhancing photoprotection.

It is an object of this invention to provide a sunscreen composition or a sunscreen enhancer comprising a UV-protecting component of one or more natural extracts, said extracts being selected from but not limited to the group consisting of: milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract.

It is another object of this invention to provide a sunscreen composition or a sunscreen enhancer comprising a UV-protecting component of one or more natural oils, said oils selected from the group consisting of but not limited to: cinnamon bark oil, vanilla oil, blue tansy oil, yarrow oil, coffee oil, cocoa oil, ravensara oil, and oils derived from grapes (hereafter referred to as "cognac oil").

It is another object of this invention to provide a sunscreen composition or a sunscreen enhancer comprising a UV-protecting component of one or more natural nutrients, said nutrients selected from the group consisting of but not limited to: Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

It is an object of this invention to provide a sunscreen composition or a sunscreen enhancer comprising a UV-protecting component of one or more natural extracts and of one or more natural oils; said extracts being selected from but not limited to the group consisting of: milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract; and said oils selected from but not limited to the group consisting of: cinnamon bark oil, cocoa oil, coffee oil, cognac oil, ravensara oil, tansy blue oil, vanilla oil and yarrow oil.

It is still another object of this invention to provide a sunscreen composition or a sunscreen enhancer comprising a UV-protecting component of one or more natural oils and of one or more natural nutrients, said oils being selected from the group consisting of but not limited to: cinnamon bark oil, cocoa oil, coffee oil, cognac oil, ravensara oil, tansy blue oil, vanilla oil and yarrow oil, and said nutrients being selected from the group consisting of but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

It is yet another object of this invention to provide a sunscreen composition or a sunscreen enhancer comprising a UV-protecting component of one or more natural extracts and one or more natural nutrients, said extracts selected from the group consisting of but not limited to milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract, and said nutrients being selected from but not limited to the group consisting of Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

It is yet another object of this invention to provide a sunscreen composition or a sunscreen enhancer comprising a UV-protecting component of one or more natural extracts, one or more natural oils and one or more natural nutrients, said extracts selected from the group consisting of but not limited to milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract; said oils selected from the group consisting of but not limited to: cinnamon bark oil, cocoa oil, coffee oil, cognac oil, ravensara oil, tansy blue oil, vanilla oil and yarrow oil; and said nutrients being selected from the group consisting of but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

A further object of the invention is to provide a method to protect skin from harmful effects of UV radiation, said method comprising applying a sunscreen comprising natural extracts and/or natural oils and/or natural nutrients as a UV-protecting component.

Still another object of this invention is to provide a method to enhance UV-protection of a sunscreen by applying on the skin a sunscreen enhancer comprising natural extracts and/or natural oils and/or natural nutrients as UV-protecting component.

DESCRIPTION OF THE PREFERRED EMBODIMENTS

The preferred embodiments of the present invention will now be described.

A natural sunscreen composition or a sunscreen enhancer according to one preferred embodiment is prepared from naturally occurring oils. The oils employed in this embodiment act as UV-protecting component of the composition and are selected from the group consisting of but not limited to cinnamon bark oil, cocoa oil, coffee oil, cognac oil, ravensara oil, tansy blue oil, vanilla oil and yarrow oil.

A natural sunscreen composition of a sunscreen enhancer according to a preferred embodiment contains one or more of the following compounds cinnamon bark oil, cocoa oil, coffee oil, cognac oil, ravensara oil, tansy blue oil, vanilla oil and yarrow oil.

A natural sunscreen composition or a sunscreen enhancer according to another preferred embodiment is prepared from natural extracts. The extracts act as UV-protecting component of the composition and are selected from the group consisting of but not limited to milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract.

A natural sunscreen composition of a sunscreen enhancer according to a preferred embodiment contains one or more of the following compounds milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract.

A natural sunscreen composition or a sunscreen enhancer according to another preferred embodiment is prepared from naturally occurring nutrients. The nutrients act as UV-protecting component of the composition and are selected from the group consisting of but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

A natural sunscreen composition of a sunscreen enhancer according to a preferred embodiment contains one or more of the following compounds Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

According to another preferred embodiment the sunscreen composition or a sunscreen enhancer contains ingredients from the group of natural oils, from the group of natural extracts and from the group of nutrients; said oils consisting of but not limited to cinnamon bark oil, cocoa oil, coffee oil, cognac oil, ravensara oil, tansy blue oil, vanilla oil and yarrow oil, said extracts consisting of but not limited to milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract and said nutrients including but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

A natural sunscreen composition of a sunscreen enhancer according to a preferred embodiment contains one or more of the following compounds from the group of natural oils: cinnamon bark oil, cocoa oil, coffee oil, cognac oil, ravensara oil, tansy blue oil, vanilla oil and yarrow oil; from the group of natural extracts: milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract; and from the group of nutrients; Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

According to other preferred embodiments the sunscreen or the sunscreen enhancer of this invention contains ingredients from the group of natural extracts and natural oils; Said extracts consisting of but not limited to milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract and said oils consisting of but not limited to cinnamon bark oil, cocoa oil, coffee oil, cognac oil, ravensara oil, tansy blue oil, vanilla oil and yarrow oil.

A natural sunscreen composition of a sunscreen enhancer according to a preferred embodiment contains one or more of the following compounds from the group of natural extracts: milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract; and from the group of natural oils: cinnamon bark oil, cocoa oil, coffee oil, cognac oil, ravensara oil, tansy blue oil, vanilla oil and yarrow oil.

According to yet another embodiment the sunscreen or the sunscreen enhancer of this invention contains ingredients from the group of natural extracts and nutrients; said extracts consisting of but not limited to milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract and said nutrients including but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

A natural sunscreen composition of a sunscreen enhancer according to a preferred embodiment contains one or more of the following compounds from the group of natural extracts: milk thistle extract, white willow extract, St John's wort extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract; and from the group of nutrients; Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

According to still another embodiment the sunscreen or the sunscreen enhancer of this invention contains ingredients from the group of natural oils and nutrients; said oils consisting of but not limited to cinnamon bark oil, cocoa oil, coffee oil, cognac oil, ravensara oil, tansy blue oil, vanilla oil and yarrow oil and said nutrients including but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

A natural sunscreen composition of a sunscreen enhancer according to a preferred embodiment contains one or more of the following compounds from the group of natural oils: cinnamon bark oil, cocoa oil, coffee oil, cognac oil, ravensara oil, tansy blue oil, vanilla oil and yarrow oil; and from the group of nutrients; Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

When the natural ingredients of this disclosure are incorporated into a sunscreen lotion base, sunscreen oil or other cosmetic formulation in described ratios and volumes, these substances act to enhance the effectiveness of any active ingredients. The natural sunscreen composition may be composed of a single one of the substances disclosed in this disclosure, or of any of the various mixtures of two or more of the substances, or of all of the substances.

The lotion base or other cosmetic formulation can be composed of any cosmetically acceptable composition. The natural sunscreen composition can be used as the only additive to the lotion base or in combination with other sunscreen actives, whether organic or inorganic, or with other natural sunscreen enhancers, such as those from natural oils, natural extracts or nutrients (vitamins, etc.).

The oil base can be composed of but not limited to butters, waxes, oils and other acceptable oil-soluble cosmetic ingredients. The natural sunscreen composition can be used as the only additive to the oil base or in combination with other suitable oils and/or sunscreen oil actives and/or natural sunscreen enhancers, such as those from natural oils, oil-soluble natural extracts or nutrients (vitamins, etc.).

The natural sunscreen enhancer can also be added to other lotions, oils, spray sunscreen formulations, lip balms, lipsticks, lipgloss, make-up or other cosmetic formulations. While sunscreen compositions with traces of natural oils added for fragrance are known, the natural oils are not used for enhancing the UV blocking activity of the sunscreen. While sunscreen compositions with traces of certain natural extracts added for fragrance or skin treatment are also known, the extracts are not used for enhancing the UV blocking activity of the sunscreen. While sunscreen compositions with nutrients such as Vitamin A, C and E added as antioxidants or skin treatments are also known, the nutrients are not used for enhancing the UV blocking activity of the sunscreen.

The compositions described here are novel and are of particular use for protecting the skin from UVA and UVB rays.

DETAILED DESCRIPTION OF THE INVENTION

The invention is now described by means of non-limiting examples.

EXAMPLE 1

Sunscreen Composition Prepared with a Mixture of Natural Oils

Sunscreen compositions were prepared with mixtures of various natural oils. The lotion base may be prepared from cosmetically acceptable ingredients including but not limited to water, an oil phase such as but not limited to natural vegetable oil with emulsifying agent. Preservatives and other additives may also be included. Natural oils for a topical sunscreen were selected from the list of ingredients shown in Table 1.

TABLE 1

| Ingredient | Source |
| --- | --- |
| Cinnamon bark oil | *Cinnamomum* sp. |
| Cocoa oil | *Theobroma cacao* |
| Coffee oil | *Coffea arabica* |
| Cognac oil | *Vitis vinifera* |
| Ravensara oil | *Ravensara aromatica* |
| Tansy blue oil | *Tanacetum annuum* |
| Vanilla oil | *Vanilla planifolia* |
| Yarrow oil | *Achillea millefolium* |

Any one or more ingredients of Table 1 may be left out, provided however, that the final composition includes 0.001-99.999% (w-%) of total oils selected from Table 1. Preferably the final composition includes 0.001-12.5% (w-%) of at least one of the oils selected from Table 1.

According to one preferred embodiment the UV-blocking component of oils for the composition are selected from Table 1 and the composition additionally includes at least one of the following ingredients: zinc oxide, titanium dioxide or any organic active sunscreen ingredients including but not limited to Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O, Trolamine salicylate in such a concentration that that the final composition is 0.001-25% (w-%) active sunscreen.

According to one preferred embodiment, the composition selected from the natural oils shown in Table 1 may also include additional natural sunscreen ingredients from natural extracts 0-36% w-%, including but not limited to white willow extract (*Salix alba*), St. John's wort extract (*Hypericum* sp.), milk thistle extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract, and grape seed extract, and/or from nutrients 0-50% w-% including but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

The sunscreen with natural oil composition selected from Table 1 may also be in a lotion base formula. The lotion base is prepared from cosmetically acceptable ingredients including but not limited to water, humectants, emollients, emulsifiers, and any additional inorganic or organic sunscreen agents or natural sunscreen ingredients.

The sunscreen with natural oil composition selected from Table 1 may also be in an oil base formula. The composition shown in Table 1 is added to an oil base appropriate for an oil sunscreen and made from cosmetically acceptable ingredients, including but not limited to emollients, butters, waxes and oils to complete the formulation along with any additional inorganic or organic sunscreen agents or natural sunscreen ingredients.

The sunscreen with natural oil composition selected from Table 1 may also be in a spray formula. The spray base is prepared from cosmetically acceptable ingredients including but not limited to water, humectants, emollients, emulsifiers, and spray-control agents and any additional inorganic or organic sunscreen agents or natural sunscreen ingredients.

The sunscreen composition with natural oil composition selected from ingredients of Table 1 may also be provided as a lip balm. The composition shown in Table 1 is added to a wax base appropriate for a lip balm and made from cosmetically acceptable ingredients, including but not limited to emollients, butters, and oils to complete the formulation along with any additional inorganic or organic sunscreen agents or natural sunscreen ingredients.

The sunscreen composition with the natural oil composition selected from ingredients of Table 1 may also be provided as a lipstick. The composition of oils selected from Table 1 is added to a wax base appropriate for a lipstick and made from cosmetically acceptable ingredients, including but not limited to emollients, colorants to complete the formulation along with any additional inorganic or organic sunscreen agents or natural sunscreen ingredients.

The sunscreen composition with the natural oil composition selected from ingredients of Table 1 may also be provided as a lipgloss. The composition of oils selected from Table 1 is in a base mixture appropriate for lip gloss made from cosmetically acceptable ingredients, including but not limited to waxes, oils, emollients, and butters, with colorants to complete the formulation along with any additional inorganic or organic sunscreen agents or natural sunscreen ingredients.

The sunscreen composition with the natural oils selected from Table 1 may also be provided as a make-up composition. The composition of oils selected from Table 1 is in a base mixture appropriate for a make-up cosmetic foundation, blush, concealer, or other type of make-up, prepared from cosmetically acceptable ingredients, including but not limited to oils and waxes, emulsifiers, water, thickeners, colorant or opacifiers, and texture agents to compete the formulation along with any additional inorganic or organic sunscreen agents or natural sunscreen ingredients.

EXAMPLE 2

Sunscreen Composition Prepared with a Mixture of Natural Extracts

Sunscreen compositions were prepared with mixtures of various natural extracts. The lotion base may be prepared from cosmetically acceptable ingredients including but not limited to water, an oil phase such as but not limited to natural vegetable oil with emulsifying agent. Preservatives and other additives may be included. Table 2 shows natural extracts for a topical sunscreen.

TABLE 2

| Ingredient | Source |
| --- | --- |
| Milk thistle extract | *Silybum* sp. |
| White willow extract | *Salix alba* |
| St John's wort extract | *Hypericum* sp. |
| *Griffonia* seed extract | *Griffonia simplicifolia* |
| *Galla chinensis* extract | *Galla chinensis* |
| Olive leaf extract | *Olea europea* |
| Hops extract | *Humus lupulus* |
| *Gentiana* extract | *Gentiana* sp. |
| Bilberry extract | *Vaccinum myrtillus* |
| *Chrysantemum* extract | *Chrysantemum* sp |
| Coptis root extrct | *Rizomna coptitis* |
| *Magnolia* bark extract | *Magnolia officinalis* |
| Rhubarb extract | *Rheum rhabarbum* |
| Red clover extract | *Trifolium pratense* |
| Rose hip extract | *Rosa* sp. |
| *Schisandra* berry extract | *Schisandra* sp. |
| Valerian root extract | *Valeriana officinalis* |
| Grape seed extract | *Vitis vinifera* |

Any one or more of the ingredients of Table 2 may be left out, provided however, that the final composition includes 0.001-99.999% (w-%) of total natural extracts selected from Table 2. Preferably the final composition includes 0.001-36% (w-%) of total natural extracts selected from Table 2.

According to one preferred embodiment the composition includes 0.001-2% (w-%) each natural extract independently selected from ingredients of Table 2.

According to one preferred embodiment the UV-blocking component of natural extracts for the composition are selected from Table 2 and the composition additionally includes at least one of the following ingredients: zinc oxide, titanium dioxide or any organic active sunscreen ingredients including but not limited to Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O, Trolamine salicylate in such a concentration that that the final composition is 0.001-25% (w-%) active sunscreen.

The composition shown in Table 2 may also include additional natural sunscreen ingredients from natural oils 0-99.998% w-% including but not limited to cinnamon bark oil, vanilla oil, blue tansy oil, yarrow oil, coffee oil, cocoa oil, ravensara oil, and cognac oil and/or nutrients 0-50% including but not limited to Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

The composition shown in Table 2 may include one or more of the following compounds cinnamon bark oil, vanilla oil, vitamin D and folic acid.

The sunscreen with natural extract composition selected from Table 2 may also be in a lotion base formula. The lotion base is prepared from cosmetically acceptable ingredients including but not limited to water, humectants, emollients, emulsifiers, and any additional inorganic or organic sunscreen agents or natural sunscreen ingredients.

The sunscreen with natural oil composition selected from oil soluble components in Table 2 may also be in an oil base formula. The composition shown in Table 2 is added to an oil base appropriate for an oil sunscreen and made from cosmetically acceptable ingredients, including but not limited to emollients, butters, waxes and oils to complete the formulation along with any additional inorganic or organic sunscreen agents or natural sunscreen ingredients.

The sunscreen with natural extract composition selected from Table 2 may also be in a spray formula. The spray base is prepared from cosmetically acceptable ingredients including but not limited to water, humectants, emollients, emulsifiers, and spray-control agents and any additional inorganic or organic sunscreen agents or natural sunscreen ingredients.

The sunscreen composition with the natural extracts selected from Table 2 may also be provided as a lip balm. The composition of natural extracts selected from Table 2 is added to a wax base appropriate for a lip balm and made from cosmetically acceptable ingredients, including but not limited to emollients, butters, and oils to complete the formulation along with any additional inorganic or organic sunscreen agents or natural sunscreen ingredients.

The sunscreen composition with the natural extracts selected from Table 2 may also be provided as a lipgloss. The composition of extracts selected from Table 2 is in a base mixture appropriate for lip gloss made from cosmetically acceptable ingredients, including but not limited to waxes, oils, emollients, and butters, with colorants to complete the formulation along with any additional inorganic or organic sunscreen agents or natural sunscreen ingredients.

The sunscreen composition with the natural extracts selected from Table 2 may also be provided as a lipstick. The composition of extracts selected from Table 2 is added to a wax base appropriate for a lip stick and made from cosmetically acceptable ingredients, including but not limited to emollients, colorants to complete the formulation along with any additional inorganic or organic sunscreen agents or natural sunscreen ingredients.

The sunscreen composition with the natural extract composition as shown in Table 2 may also be provided as a make-up composition. The composition shown in Table 2 is in a base mixture appropriate for a make-up cosmetic foundation, blush, concealer, or other type of make-up, prepared from cosmetically acceptable ingredients, including but no limited to oils and waxes, emulsifiers, water, thickeners, colorant or opacifiers, and texture agents to compete the formulation along with any additional inorganic or organic sunscreen agents or natural sunscreen ingredients.

EXAMPLE 3

Sunscreen Composition Prepared with a Mixture of Nutrients

Sunscreen compositions were prepared with mixtures of various nutrients. The lotion base may be prepared from cosmetically acceptable ingredients including but not limited to water, an oil phase such as but not limited to natural vegetable oil with emulsifying agent. Preservatives and other additives may be included. Table 3 shows one preferred composition of nutrients for a topical sunscreen.

TABLE 3

| Ingredient | Preferred source |
| --- | --- |
| Vitamin D | — |
| Folic acid (vitamin B9) | *Spinacia oleracea* |
| Riboflavin (Vitamin B2) | Genus *Triticum* |
| Pyridoxine (Vitamin B6) | Genus *Triticum* |
| Cyanocobalmine (Vitamin B12) | *Arthrospira platensis* and *Arthrospira maxima* |
| Collagen or partially | — |

TABLE 3-continued

| Ingredient | Preferred source |
| --- | --- |
| hydrolyzed collagen or related substances | |
| Silk protein or partially hydrolyzed silk protein or related substances | — |
| thymine | — |
| adenine | — |
| cytosine | — |
| guanine | — |
| rutin | *Carpobrotus edulis* |
| quercetin | *Nasturtium officinale* |
| azalein | *Plumbago* sp. or *Rhododendron* sp. |
| hyperocide | *Hypercium perforatum* |
| isoquercetin | *Mangifera indica* or *Rheum nobile* |
| kaempferitrin | *Hedvotis verticillata* |
| myricitin | Genus *Juglans* |
| robinin | *Vinca erecta* or *Robinia pseudoacacia* |
| spiraeoside | *Filipendula ulmaria* or *Allium cepa* |
| xanthorhamin | Genus *Rhamnus* |
| icariin | *Epimedium* sp. |
| truxerutin | *Sophora japonica* |
| Vitamin K | *Brassica oleracea* or *Spinacia oleracea* |
| Coenzyme Q | *Glycine max* |

All the nutrients listed in Table 3 are natural compounds and several of them are present in specific plant species, which are listed in the table as preferred source. As the structures of these nutrients are known they may alternatively be chemically synthesized.

Any one or more of the ingredients in Table 3 may be left out, provided however the final composition includes 0.001-99.999 w-% of total nutrients. Preferably, the final composition includes 0.001-50 w-% of total nutrients.

According to one preferred embodiment the composition includes 0.001-2 w-% each nutrient independently selected from ingredients of Table 3.

According to one preferred embodiment the UV-blocking component of nutrients for the composition are selected from Table 3 and the composition additionally includes at least one of the following ingredients: zinc oxide, titanium dioxide or any organic active sunscreen ingredients including but not limited to Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O, Trolamine salicylate in such a concentration that that the final composition is 0.001-25 w-% active sunscreen.

The composition shown in Table 3 may also include additional natural sunscreen ingredients from natural oils 0-99.998 w-% including but not limited to cinnamon bark oil, vanilla oil, blue tansy oil, yarrow oil, coffee oil, cocoa oil, ravensara oil, and cognac oil and/or from natural extracts 0-36 w-%, including but not limited to white willow extract (*Salix alba*), St. John's wort extract (*Hypericum* sp.), milk thistle extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract The sunscreen with nutrient composition selected from Table 3 may also be in a lotion base formula. The lotion base is prepared from cosmetically acceptable ingredients including but not limited to water, humectants, emollients, emulsifiers, and any additional inorganic or organic sunscreen agents or natural sunscreen ingredients.

The sunscreen with nutrient composition selected from oil soluble components in Table 3 may also be in an oil base formula. The composition shown in Table 3 is added to an oil base appropriate for an oil sunscreen and made from cosmetically acceptable ingredients, including but not limited to emollients, butters, waxes and oils to complete the formulation along with any additional inorganic or organic sunscreen agents or natural sunscreen ingredients.

The sunscreen with nutrient composition as shown in Table 3 may also be in a spray formula. The spray base is prepared from cosmetically acceptable ingredients including but not limited to water, humectants, emollients, emulsifiers, and spray-control agents and any additional inorganic or organic sunscreen agents or natural sunscreen ingredients.

The sunscreen composition with the nutrient composition as shown in Table 3 may also be provided as a lip balm. The composition shown in Table 3 is added to a wax base appropriate for a lip balm and made from cosmetically acceptable ingredients, including but not limited to emollients, butters, and oils to complete the formulation along with any additional inorganic or organic sunscreen agents or natural sunscreen ingredients.

The sunscreen composition with the nutrient composition as shown in Table 3 may also be provided as a lipgloss. The composition shown in Table 3 is in a base mixture appropriate for lip gloss made from cosmetically acceptable ingredients, including but not limited to waxes, oils, emollients, and butters, with colorants to complete the formulation along with any additional inorganic or organic sunscreen agents or natural sunscreen ingredients.

The sunscreen composition with the nutrient composition as shown in Table 3 may also be provided as a lipstick. The composition shown in Table 3 is added to a wax base appropriate for a lipstick and made from cosmetically acceptable ingredients, including but not limited to emollients, colorants to complete the formulation along with any additional inorganic or organic sunscreen agents or natural sunscreen ingredients.

The sunscreen composition with the nutrient composition as shown in Table 3 may also be provided as a make-up composition. The composition shown in Table 3 is in a base mixture appropriate for a make-up cosmetic foundation, blush, concealer, or other type of make-up, prepared from cosmetically acceptable ingredients, including but no limited to oils and waxes, emulsifiers, water, thickeners, colorant or opacifiers, and texture agents to compete the formulation along with any additional inorganic or organic sunscreen agents or natural sunscreen ingredients.

EXAMPLE 4

Sunscreen Composition Prepared with Natural Extracts, Natural Oils and Nutrients Sunscreen compositions were prepared with natural extracts, natural oils and nutrients. The lotion base may be prepared from cosmetically acceptable ingredients including but not limited to water, an oil phase such as but not limited to natural vegetable oil with emulsifying agent. Preservatives and other additives may be included. Table 4 shows a composition of topical sunscreen prepared with natural extracts, natural oils and nutrients.

TABLE 4

| Ingredient | Concentration (w-%) |
|---|---|
| Cinnamon bark oil | 0.001-1.7999% |
| Cocoa oil | 0.001-1.7999% |
| Coffee oil | 0.001-1.7999% |
| Cognac oil | 0.001-1.7999% |
| *Ravensara* oil | 0.001-1.7999% |
| Tansy blue oil | 0.001-1.7999% |
| Vanilla oil | 0.001-1.7999% |
| Yarrow oil | 0.001-1.7999% |
| Milk thistle extract | 0.001-2% |
| White willow extract | 0.001-2% |
| St. John's wort extract | 0.001-2% |
| *Griffonia* seed extract | 0.001-2% |
| *Galla chinensis* extract | 0.001-2% |
| Olive leaf extract | 0.001-2% |
| Hops extract | 0.001-2% |
| Gentian extract | 0.001-2% |
| Bilberry extract | 0.001-2% |
| *Chrysantemum* extract | 0.001-2% |
| Coptis root extract | 0.001-2% |
| *Magnolia* bark extract | 0.001-2% |
| Rhubarb extract | 0.001-2% |
| Red clover extract | 0.001-2% |
| Rose hip extract | 0.001-2% |
| *Schisandra* berry extract | 0.001-2% |
| Valerian root extract | 0.001-2% |
| Grape seed extract | 0.001-2% |
| Vitamin D | 0.001-2% |
| Folic acid (vitamin B9) | 0.001-2% |
| Riboflavin (Vitamin B3) | 0.001-2% |
| Pyridoxine (Vitamin B6) | 0.001-2% |
| Cyanocobalmine (Vitamin B12) | 0.001-2% |
| Collagen or partially hydrolyzed collagen or related substances | 0.001-2% |
| Silk protein or partially hydrolyzed silk protein or related substances | 0.001-2% |
| thymine | 0.001-2% |
| adenine | 0.001-2% |
| cytosine | 0.001-2% |
| guanine | 0.001-2% |
| rutin | 0.001-2% |
| quercetin | 0.001-2% |
| azalein | 0.001-2% |
| hyperocide | 0.001-2% |
| isoquercetin | 0.001-2% |
| kaempferitrin | 0.001-2% |
| myricitin | 0.001-2% |
| robinin | 0.001-2% |
| spiraeoside | 0.001-2% |
| xanthorhamin | 0.001-2% |
| icariin | 0.001-2% |
| truxerutin | 0.001-2% |
| Vitamin K | 0.001-2% |
| Coenzyme Q | 0.001-2% |

Any one or more of the ingredients in table 4 may be left out, however the final composition includes 0.001-99.999 w-% mixture of the one or more natural extract, one or more natural oils and one or more nutrients wherein, the composition includes 0.001-36 w-% natural extract(s), 0.001-14.392 w-% natural oil(s) and 0.001-49.5998 w-% nutrients.

According to one preferred embodiment the UV-blocking component for the composition are selected from Table 4 and the composition additionally includes at least one of the following ingredients: zinc oxide, titanium dioxide or any organic active sunscreen ingredients including but not limited to Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O, Trolamine salicylate in such a concentration that that the final composition is 0.001-25 w-% active sunscreen.

The sunscreen with natural extracts, natural oils and nutrient composition selected from Table 4 may also be in a lotion base formula. The lotion base is prepared from cosmetically acceptable ingredients including but not limited to water, humectants, emollients, emulsifiers, and any additional inorganic or organic sunscreen agents or natural sunscreen ingredients.

The sunscreen with natural extracts, natural oils and nutrient composition selected from oil soluble components in Table 4. The composition shown in Table 4 is added to an oil base appropriate for an oil sunscreen and made from cosmetically acceptable ingredients, including but not limited to emollients, butters, waxes and oils to complete the formulation along with any additional inorganic or organic sunscreen agents or natural sunscreen ingredients.

The sunscreen with natural extracts, natural oils and nutrient composition as shown in Table 4 may also be in a spray formula. The spray base is prepared from cosmetically acceptable ingredients including but not limited to water, humectants, emollients, emulsifiers, and spray-control agents and any additional inorganic or organic sunscreen agents or natural sunscreen ingredients.

The sunscreen composition with natural extracts, natural oils and nutrient composition as shown in Table 4 may also be provided as a lip balm. The composition shown in Table 4 is added to a wax base appropriate for a lip balm and made from cosmetically acceptable ingredients, including but not limited to emollients, butters, and oils to complete the formulation along with any additional inorganic or organic sunscreen agents or natural sunscreen ingredients.

The sunscreen composition with natural extracts, natural oils and nutrient composition as shown in Table 4 may also be provided as a lipgloss. The composition shown in Table 4 is in a base mixture appropriate for lipgloss made from cosmetically acceptable ingredients, including but not limited to waxes, oils, emollients, and butters, with colorants to complete the formulation along with any additional inorganic or organic sunscreen agents or natural sunscreen ingredients.

The sunscreen composition with natural extracts, natural oils and nutrient composition as shown in Table 4 may also be provided as a lipstick. The composition shown in Table 4 is added to a wax base appropriate for a lipstick and made from cosmetically acceptable ingredients, including but not limited to emollients, colorants to complete the formulation along with any additional inorganic or organic sunscreen agents or natural sunscreen ingredients.

The sunscreen composition with natural extracts, natural oils and nutrient composition as shown in Table 4 may also be provided as a make-up composition. The composition shown in Table 4 is in a base mixture appropriate for a make-up cosmetic foundation, blush, concealer, or other type of make-up, prepared from cosmetically acceptable ingredients, including but no limited to oils and waxes, emulsifiers, water, thickeners, colorant or opacifiers, and texture agents to compete the formulation along with any additional inorganic or organic sunscreen agents or natural sunscreen ingredients.

The sunscreen composition according to any one of the embodiments of this disclosure is to applied to skin before exposure to sun light for protection against the harmful effects of UV radiation.

The advantages of the present invention include, without limitation, natural sunscreen formulation enhancement based on natural oils, natural extracts, and nutrients that either do not have the undesirable side effects of the synthetic sunscreen agents, or have such side effects in reduced amounts, while still providing protection from the damaging effects of the sun's radiation. Through reducing these undesirable side effects, this invention yields improved human health and safer environments through reduced organic compound use.

In broad embodiment, the present invention is a cosmetic composition with the activity of a sunscreen or sunscreen enhancer prepared from natural oils, natural extracts, and nutrients.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A sunscreen composition comprising an effective amount of a UV-protecting component, said UV-protecting component comprising a combination of: milk thistle extract, white willow extract, St John's worth extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract and grape seed extract, wherein the composition comprises up to 36 w-% of the extracts and wherein the concentration of each extract is independently between 0.001 and 2 w-%.

2. The composition of claim 1, wherein the composition additionally comprises 0.001-25 w-% of active sunscreen ingredients, said ingredients selected from the group consisting of zinc oxide, titanium dioxide, and organic active sunscreen ingredients.

3. The composition of claim 2, wherein the organic active sunscreen ingredients are selected from the group consisting of Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O and Trolamine salicylate.

4. The composition of claim 1, wherein the composition additionally comprises one or more natural oils selected from the group consisting of cinnamon bark oil, cocoa oil, coffee oil, cognac oil, ravensara oil, tansy blue oil, vanilla oil and yarrow oil or one or more nutrients selected from the group consisting of Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

5. The composition of claim 1, wherein the composition is in the form of a topical lotion, an oil, a spray, a lip balm, a make-up cream or any other acceptable cosmetic composition.

6. A sunscreen composition comprising an effective amount of a UV-protecting component, said UV-protecting component comprising a combination of natural oils comprising cinnamon bark oil, cocoa oil, coffee oil, cognac oil, ravensara oil, tansy blue oil, vanilla oil and yarrow oil, wherein the total concentration of natural oils is 0.001-99.999 w-% and wherein the concentration of each natural oil is independently between 0.001 and 12.5 w-%.

7. The composition of claim 6, wherein the composition additionally comprises 0.001-25 w-% of active sunscreen ingredients, said ingredients selected from one or more of the group consisting of zinc oxide, titanium dioxide, and organic active sunscreen ingredients.

8. The composition of claim 7, wherein the organic active sunscreen ingredients are selected from the group consisting of Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O and Trolamine salicylate.

9. The composition of claim 6, wherein the composition additionally comprises one or more plant extracts selected from the group consisting of white willow extract (*Salix alba*), St. John's wort extract (*Hypericum* sp.), milk thistle extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract, and grape seed extract, or one or more nutrients selected from the group consisting of Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q.

10. The composition of claim 9, wherein the total concentration of extracts is 0.001-36 w-% and the total concentration of nutrients is 0-50 w-%.

11. The composition of claim 6, wherein the composition is in the form of topical lotion, oil, a spray, a lip balm, a make-up cream or any other acceptable cosmetic composition.

12. A sunscreen composition comprising an effective amount of a UV-protecting component, said UV-protecting component comprising a combination of the following nutrients: Vitamin D, Folic acid, riboflavin, pyridoxine, cyanocobalamine, collagen or partially hydrolyzed collagen, silk protein or partially hydrolyzed silk protein, thymine, cytosine, adenine, guanine, rutin, quercetin, azalein, hyperoside, isoquercetin, kampferitin, myricitrin, robinin, speraeoside, xanthorhamin, icariin, truxrutin, vitamin K and coenzyme Q,
wherein the total concentration of the combination of nutrients is 0.001-50 w-% and the concentration of each nutrient is independently between 0.001 and 2 w-%.

13. The composition of claim 12, wherein the composition additionally comprises 0.001-25 w-% of active sunscreen ingredients, said ingredients selected from the group consisting of zinc oxide, titanium dioxide, and organic active sunscreen ingredients.

14. The composition of claim 13, wherein the organic active sunscreen ingredients are selected from the group consisting of Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O and Trolamine salicylate 15. The composition of claim 12, wherein the composition additionally comprises one or more natural oils selected from the group consisting of cinnamon bark oil, cocoa oil, coffee oil, cognac oil, ravensara oil, tansy blue oil, vanilla oil and yarrow oil, or one or more plant extracts selected from the group consisting of white willow extract (*Salix alba*), St. John's wort extract (*Hypericum* sp.), milk thistle extract, griffonia seed extract, *Galla chinensis* extract, olive leaf extract, hops extract, gentian extract, bilberry extract, chrysanthemum extract, coptis root extract, magnolia bark extract, rhubarb extract, red clover extract, rose hip extract, schisandra berry extract, valerian root extract, and grape seed extract.

16. The composition of claim 15, wherein the total concentration of natural oils are is 0-99.999 w-% and the total concentration of nutrients is 0-50 w-%.

17. The composition of claim 12, wherein the composition is in the form of a topical lotion, an oil, a spray, a lip balm, a make-up cream or any other acceptable cosmetic composition.

18. A sunscreen composition comprising an effective amount of a UV-protecting component, wherein said UV-protecting component comprises a combination of plant extracts, a combination of natural oils and a combination of nutrients, said combination of extracts consisting of 0.001-2 w-% milk thistle extract, 0.001-2 w-% white willow extract, 0.001-2 w-% St John's wort extract, 0.001-2 w-% griffonia seed extract, 0.001-2 w-% *Galla chinensis* extract, 0.001-2 w-% olive leaf extract, 0.001-2 w-% hops extract, 0.001-2 w-% gentian extract, 0.001-2 w-% bilberry extract, 0.001-2 w-% chrysanthemum extract, 0.001-2 w-% coptis root extract, 0.001-2 w-% magnolia bark extract, 0.001-2 w-% rhubarb extract, 0.001-2 w-% red clover extract, 0.001-2 w-% rose hip extract, 0.001-2 w-% schisandra berry extract, 0.001-2 w-% valerian root extract and 0.001-2 w-% grape seed extract, wherein total concentration of the extracts is 0.001-36 w-%; said combination of oils consisting of: 0.001-1.7999 w-% of cinnamon bark oil, 0.001-1.7999 w-% cocoa oil, 0.001-1.7999 w-% coffee oil, 0.001-1.7999 w-% cognac oil, 0.001-1.7999 w-% ravensara oil, 0.001-1.7999 w-% tansy blue oil, 0.001-1.7999 w-% vanilla oil and 0.001-1.7999 w-% yarrow oil; wherein total concentration of oils is 0.001-14.3992 w-%; and said combination of nutrients consisting of: 0.001-1.7999 w % Vitamin D, 0.001-2 w % Folic acid, 0.001-2 w % riboflavin, 0.001-2 w % pyridoxine, 0.001-2 w % cyanocobalamine, 0.001-2 w % collagen or partially hydrolyzed collagen, 0.001-2 w % silk protein or partially hydrolyzed silk protein, 0.001-2 w % thymine, 0.001-2 w % cytosine, 0.001-2 w % adenine, 0.001-2 w % guanine, 0.001-2 w % rutin, 0.001-2 w % quercetin, 0.001-2 w % azalein, 0.001-2 w % hyperoside, 0.001-2 w % isoquercetin, 0.001-2 w % kampferitin, 0.001-2 w % myricitrin, 0.001-2 w % robinin, 0.001-2 w % speraeoside, 0.001-2 w % xanthorhamin, 0.001-2 w % icariin, 0.001-2 w % truxrutin, 0.001-1.7999 w % vitamin K and 0.001-2 w % coenzyme Q, wherein total concentration of nutrients is 0.001-49.5998% (w-%).

19. The composition of claim 18 wherein the composition additionally comprises 0.001-25 w-% of active sunscreen ingredients, said ingredients selected from the group consisting of zinc oxide, titanium dioxide, and organic active sunscreen ingredients.

20. The composition of claim 19, wherein the organic active sunscreen ingredients are selected from the group consisting of Avobenzone, Dioxybenzone, Ecamsule, Meradimate, Oxybenzone, Sulisobenzone, Cinoxate, Ensulizole, Homosalate, Octinoxate, Octisalate, Octocrylene PABA, Padimate O and Trolamine salicylate.

21. The composition of claim 18, wherein the composition is in the form of a topical lotion, an oil, a spray, a lip balm, a make-up cream or any other acceptable cosmetic composition.

* * * * *